United States Patent [19]

Kim et al.

[11] Patent Number: 5,755,738
[45] Date of Patent: May 26, 1998

[54] AUTOMATIC SENSING LEVEL ADJUSTMENT FOR IMPLANTABLE CARDIAC RHYTHM MANAGEMENT DEVICES

[75] Inventors: Jungkuk Kim, Roseville; Qingsheng Zhu, Little Canada, both of Minn.

[73] Assignee: Cardiac Pacemakers, Inc., St. Paul, Minn.

[21] Appl. No.: 840,994

[22] Filed: Apr. 22, 1997

[51] Int. Cl.[6] ............................................. A61N 1/365
[52] U.S. Cl. ............................................. 607/9
[58] Field of Search ............................................. 607/9, 27

[56] References Cited

U.S. PATENT DOCUMENTS 5,564,430 10/1996 Jacobson et al. ................... 128/697

Primary Examiner—William E. Kamm
Attorney, Agent, or Firm—Haugen and Nikolai, P.A.

[57] ABSTRACT

An implantable cardiac rhythm management device 10 includes a microprocessor-based controller 28 adapted to receive digitized electrogram signals from leads 14 placed on or in the heart and incorporates an autosense algorithm which is called into play when an electrogram is detected that exceeds an event detect threshold ET and capable of adjusting a sensing threshold ST to improve detection of cardiac depolarization signals in the presence of noise. The sensing threshold is automatically set on a beat-to-beat basis at a level that is dependent on a predetermined percentage of the peak amplitude of a current and an immediately preceding sensed or paced beat. The event threshold ET, which is always set at 50% of the sensing threshold, provides noise discrimination. The predetermined percentage value applied to the average peak value in arriving at the sensing threshold ST is dependent upon relative amplitudes of electrogram excursions and the signal-to-noise ratio encountered.

16 Claims, 12 Drawing Sheets

AUTOMATIC SENSING LEVEL ADJUSTMENT FOR IMPLANTABLE CARDIAC RHYTHM MANAGEMENT DEVICES

BACKGROUND OF THE INVENTION

I. Field of the Invention

This invention relates generally to apparatus for stimulating cardiac tissue, and more particularly to an apparatus and method for automatically adjusting the sensing threshold of such apparatus for detecting cardiac depolarization signals in the presence of noise.

II. Discussion of the Prior Art

For the most part,prior art implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implanted pulse generator. Typically, the signals emanating from the sense amplifier are applied to one input of a comparator circuit whose other input is connected to a source of reference potential. Only when an electrogram signal from the sense amplifier exceeds the reference potential threshold will it be treated as a cardiac paced or sensed beat.

In the case of a programmable cardiac rhythm management device, the prescribing physician can change the threshold potential of the comparator, but in spite of the flexibility which the programmable threshold offers, malsensing will still occur frequently enough to result in patient discomfort. This may be due to the fact that cardiac depolarization events (intrinsic beats) can result in widely different peak amplitudes, depending on patient activity, body position, drugs being used, etc. The peak amplitudes of the electrogram signals associated with cardiac depolarization events is also quite dependent on the type of lead being used and whether the electrodes on the lead abut cardiac tissue or are floating within a cardiac chamber. Thus, it is desirable that an implantable pacemaker or defibrillator be able to use active or passive fixation bipolar and unipolar leads and by single pass VDD or DDD leads. When the peak amplitudes associated with cardiac depolarization events become too small relative to a programed threshold or noise levels in the electrogram increase, the likelihood of false sensing increases.

The Jacobson et al. U.S. Pat. No. 5,564,430 describes an automatic sensing threshold control for implantable cardiac rhythm management devices. In the device described in that patent, the sensing threshold is set according to the amplitude of both sensed signals corresponding to cardiac activity and to sensed noise with the algorithm adjusting the threshold on a beat-to-beat basis such that the sensing threshold is substantially below the peak amplitude of sensed cardiac activity, but above the noise level. In accordance with that patent, the sensing threshold is initially set at a predetermined fraction (one-fourth) of a measured sensed depolarization signal. An absolute refractory period following the occurrence of a sensed signal is provided for and following the absolute refractory period is an established "noise refractory period". If a sensed signal that exceeds the set sensing threshold is detected during the noise refractory period, the noise refractory period is restarted and the sensing threshold is incremented by increasing its level by about 0.2 millivolts such that the resulting sensing threshold will ultimately be set above the noise amplitude.

While the method described in the Jacobson et al. patent may prove satisfactory for robust electrogram signals, it is less than satisfactory for low amplitude electrograms, such as may be associated with the use of single pass SVDD or SDDD leads and low amplitude atrial electrograms derived from conventional leads. A further drawback of the algorithm described in the Jacobson et al. '430 patent is the noise detection utilizing retriggerable noise refractory windows. If noise signals are stable in amplitude, the algorithm will detect noise levels properly. However, those skilled in the art appreciate that noise does not behave in that fashion. The amplitude of the noise level keeps changing and often includes impulsive noise excursions. It is, therefore, difficult for a noise refractory window to detect episodes of that type. Also, the 0.2 millivolt buffering between noise and the sensing threshold may not be sufficient in many situations.

A need, therefore, exists for an autosense algorithm for incorporation into a microprocessor-based cardiac rhythm management device that will provide automatic adjustment of the sensed threshold, taking into account noise levels encountered and the amplitude of electrogram signals associated with sensed events. The present invention meets that need.

SUMMARY OF THE INVENTION

The present invention provides a method and apparatus for automatically adjusting a sensing threshold (ST) in a cardiac rhythm management device to distinguish cardiac depolarization events from noise in cardiac electrogram signals. The apparatus includes a sensing amplifier for amplifying and filtering cardiac electrogram signals picked up on electrodes and coupled to the sense amplifier by a pacing lead. Also included is a microprocessor-based controller coupled to receive the sensed electrogram signals and means controlled by the microprocessor-based controller for applying cardiac stimulation pulses to a patient's heart in response to control signals from the microprocessor-based controller on a beat-to-beat basis. The algorithm or method in accordance with the present invention includes the steps of calculating in the microprocessor-based controller an average of the peak amplitudes of the two most recent cardiac electrogram signals and then establishing a ST value equal to a predetermined percentage of the average of peak values so calculated. An event threshold (ET) is also established that is a predetermined percentage of the ST value. A peak amplitude of a next subsequent cardiac electrogram signal is compared to the ET value and if that peak amplitude exceeds the ET value, the microprocessor of the microprocessor-based controller is interrupted to initiate a programmed subroutine for determining if that subsequent cardiac electrogram signal also exceeds the ST value. If so, that event is identified as a cardiac depolarization event rather than noise. The above procedure is repeated on a beat-to-beat basis whereby new ST and ET values are repeatedly calculated to be used in distinguishing a next cardiac depolarization event from noise.

The autosense algorithm of the present invention may have a plurality of modes, each defining a different percentage of the average peak amplitude of a current and an immediately preceding electrogram excursion that the ST can be set at. The particular mode selected is determined by detected noise levels relative to the ET.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
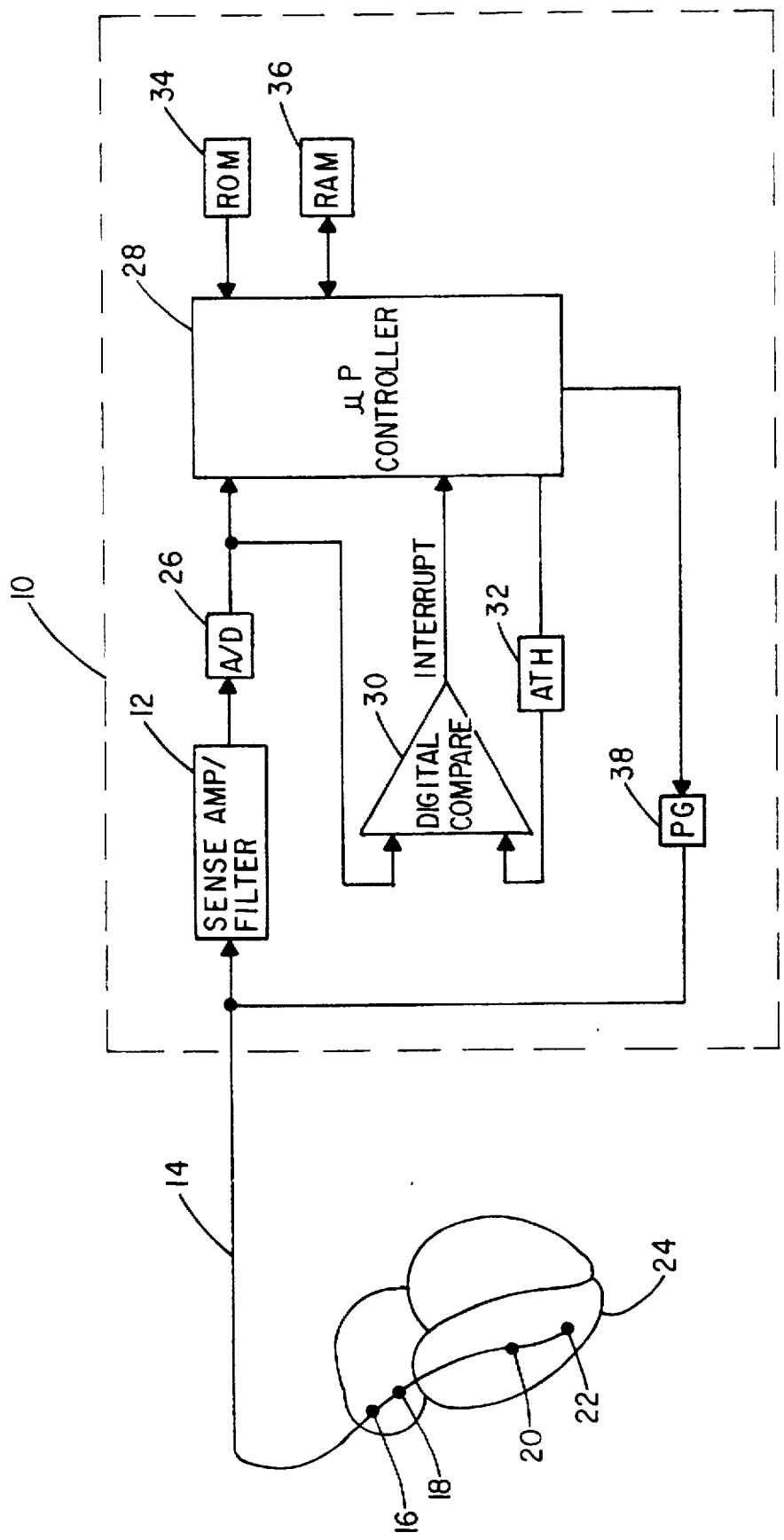
FIG. 1 is a general block diagram of a cardiac rhythm management device incorporating the autosensing feature of the present invention.

Referring first to FIG. 1, there is illustrated by means of a block diagram, the hardware platform in which the autosense algorithm of the present invention is utilized. Shown enclosed by the broken line box 10 is the circuitry for implementing a cardiac rhythm management device, such as a bradycardia pacemaker. It is seen to include a sense amplifier/filter 12 having its input connected by a pacing lead 14 to a plurality of electrodes 16–22 disposed on or in the heart 24. In the drawing of FIG. 1, the lead comprises a bipolar single pass VDD or DDD lead, various forms of which are known to those skilled in the art. The electrodes 20 and 22 are designed to detect ventricular depolarizations while electrodes 16 and 18 sense atrial depolarizations.

The output from the sense amp/filter circuit 12 is applied to an analog-to-digital converter 26 which converts the detected electrogram signals emanating from the sense amplifier/filter circuit 12 to corresponding digital values compatible with a microprocessor-based controller 28.

The output from the A/D converter 26 is also applied as a first input to a digital comparator 30. The reference input to the comparator 30 is a digital value stored in the ATH register 32 and that value is periodically computed during execution of the algorithm by the microprocessor 28 for entry into the register 32.

Also associated with the microprocessor 28 is a ROM memory 34 for storing programs to be executed by the microprocessor-based controller 28. Likewise, a RAM memory 36 is provided for storing operands used in carrying out the computations by the microprocessor-based controller.

The microprocessor-based controller provides a control output to a pulse generator 38 at appropriate times and the resulting pulses are applied over the lead 14 to the electrodes 16, 18, 20 and 22 for providing electrical stimulation to the heart 24.

The drawing of FIG. 1 shows only one hardware configuration in which the autosense algorithm of the present invention can be implemented. Those skilled in the art can appreciate that the circuit of FIG. 1 can be modified so that the digital comparator 30 and ATH register 32 can be internal to the microprocessor-based controller 28. It is also possible to add an additional digital comparator in parallel with the digital comparator 30 and provide a separate threshold register 32 for containing a value for ST rather than time sharing the digital comparator 30 between the detection of electrogram excursions that exceed the event threshold and those that exceed the sense threshold which is the configuration contemplated by the embodiment illustrated in FIG. 1.

Those skilled in the art will also appreciate that the arrangement shown in FIG. 1 can be used for sensing both intrinsic P-waves and R-waves as well as applied pacing pulses. In that P-wave signals in the electrogram tend to be of significantly smaller peak value than R-wave excursions, the present invention will be described as involving the sensing of P-wave activity but, of course, the autosense algorithm to be described herein can be used for the detection of R-wave activity as well.

The operation of the autosense algorithm of the present invention is based upon three parameters: (1) peak amplitude of two previous beats, (2) existing noise level, and (3) signal-to-noise ratio (SNR). To be classified as a cardiac beat (P-wave or R-wave), a sensed deflection should be higher than a sensing threshold (ST) determined by two previous beats and noise level and, at the same time, should have a SNR greater than 2. In achieving automatic sensitivity control, the algorithm uses the average of the peak amplitudes of two most recent P-waves and any noise excursions that are higher than 50% of the preceding sensing threshold to determine a new sensing threshold. Moreover, the updating of sensing threshold is done on a beat-by-beat basis.

Figure 2:
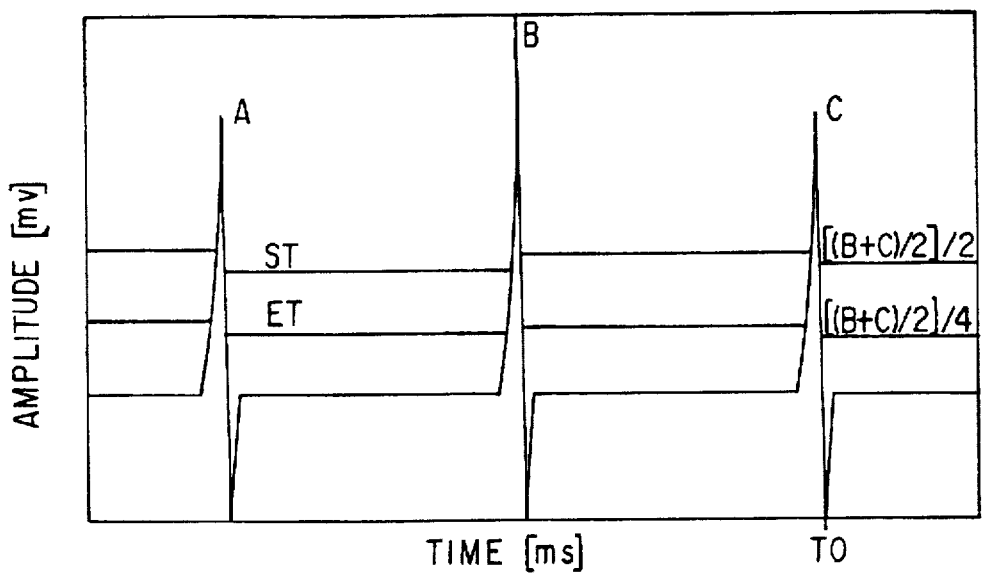
FIG. 2 is an electrogram showing the manner in which the sensing threshold (ST) and the event threshold (ET) are determined.

Referring to FIG. 2. there is shown an electrogram that is included herein for definitional purposes. In this figure. excursions B and C are the two most recent peak amplitudes that are averaged and the sensing threshold is shown as being set at 50% of that average. The event threshold is always set at 50% of the sensing threshold. The event threshold is computed by the microprocessor 28 on a beat-to-beat basis and entered into the register 32. When a deflection, such as is labeled "C" in the electrogram, exceeds the event threshold (ET), the comparator 30 generates an interrupt to the microprocessor 28 causing the microprocessor to execute a routine that checks to determine if the deflection C is higher than the sensing threshold ST. If the peak of the deflection C is higher than the sensing threshold ST, the microprocessor will treat excursion C as a P-wave and then will calculate a new ST value based on that peak and the immediately preceding peak (B).

Figure 3:
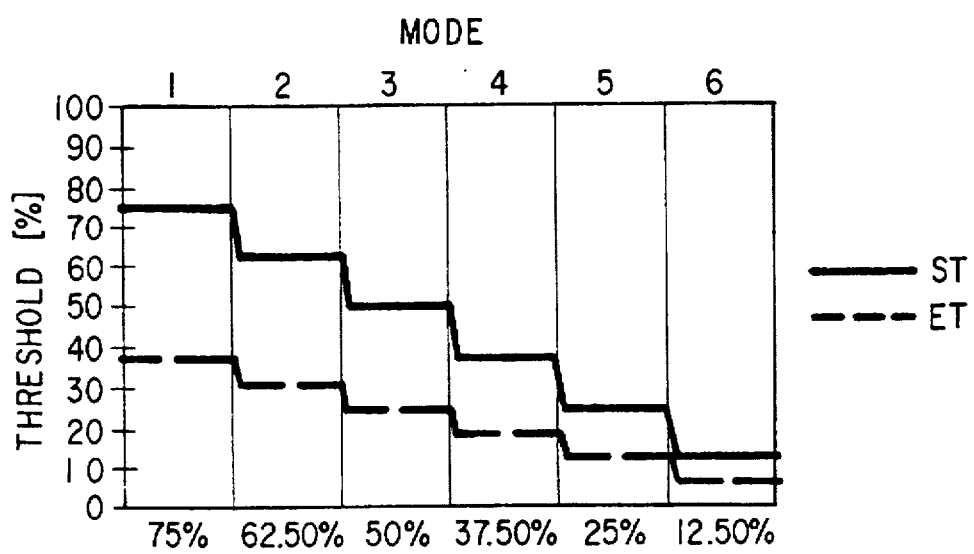
FIG. 3 is a graph showing ST and ET values for a plurality of different ST_modes.

In order to take into account noise levels, the autosense algorithm of the present invention contemplates that the percentage value to be used in arriving ST can fall into any of a plurality of zones or modes. Referring to FIG. 3. there is a plot showing the percentage value by which the average peak amplitudes of the two previous beats are to be multiplied in arriving at ST. ET is always one-half of ST. As seen in this plot, when in mode 1, the multiplication factor is 0.75, in mode 2 is 0.625, in mode 3 is 0.5, in mode 4 is 0.375, in mode 5 is 0.25 and in mode 6 is 0.125. These percentage values are conveniently chosen to be obtained by shift right, shift left and add operations inside the microprocessor 28. This obviates the need for otherwise computation intensive calculations. The nominal percentage value for sensed events is mode 4 and during paced events is mode 5. However, when the nominal sensing thresholds are too high or too low compared to noise levels, the sensing mode is automatically changed for proper operation.

During normal sensing events, the autosense algorithm herein described chooses one of mode 1, mode 2, mode 3 or mode 4 and tries to converge to the nominal mode, i.e., mode 4, which sets the sensing threshold at 37.5% of the averaged amplitude of the two most recently occurring beats. When noise amplitudes exceeding ET are sensed, the algorithm raises ST and ET follows at 50% of ST. The raising of the ET threshold provides increased noise immunity. If the new ET threshold does not detect noise events exceeding it, the algorithm automatically switches to a next lower mode and then again determines if the noise is still present. If still there, the algorithm again raises the ST threshold. If not, the algorithm selects the mode that is one step lower until it converges to the nominal mode (mode 4).

Embodied in the microprocessor 28 is a P—P interval counter capable of measuring the length of time between two successive P-wave excursions in the electrogram. When the P—P interval counter times out, an interrupt is generated to the microprocessor 28 causing it to execute a program that issues a pacing pulse via pulse generator 38 and simultaneously initiates another feature of the autosense algorithm of the present invention. In this case, the algorithm attempts to force the sensing mode to mode 5, i.e., 25% of the average peak value of the proceeding two excursions.

As will be explained in greater detail below when the flow charts defining the autosense algorithm are described in detail, the algorithm attempts to maintain mode 5 operation during pacing events. In fact, mode 5 and mode 6 are reserved for pacing events and are not used for sensed events. Mode 4 can only be reached for paced events when a peak amplitude of a current P-wave is greater than twice the sensing threshold ST. By providing such a measure, a situation is prevented in which the next sensing threshold is calculated based upon a very low P-wave detected by a low sensing threshold (mode 5 or mode 6) during pacing events.

Figure 4:
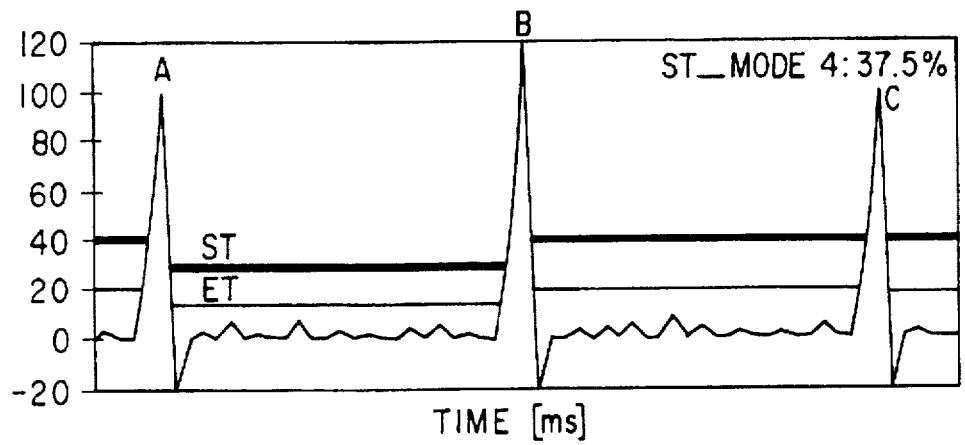
FIG. 4 is an electrogram illustrating conditions under which the autosense algorithm sets the mode when the average of the two most recent beats have a robust amplitude and the noise level is low.

To better understand the operation of the autosense algorithm of the present invention, it is deemed expedient to provide a number of different examples showing how automatic mode changing occurs as a function of average peak amplitude of two previous beats and the level of noise that may exist. The first situation to be considered is where continuous intrinsic beat detection takes place and where the P-wave amplitudes are robust and the noise level remains lower than the event threshold, ET. The electrogram for this situation is illustrated in FIG. 4. In this case, the algorithm calculates the next sensing thresholds based on the average amplitude of a current and a preceding beat and the percentage of the averaged amplitude for ST is chosen as one of the first four modes illustrated in FIG. 3 automatically by considering the current mode and noise level. If the noise level is lower than ET and the current ST_mode is not mode 4, the algorithm will automatically choose one step lower until ST_mode 4 is reached. If the current mode happens to be mode 4, the algorithm will remain in that mode until pacing is required or noise exceeding ET is detected.

If the noise level exceeds ET, but the SNR of a deflection exceeding ST is greater than 2, the excursion will be accepted as a P-wave and the next higher sensing level will be chosen. This type of operation is illustrated graphically in the electrogram of FIG. 5. In this figure, several excursions between peaks A and B exceed ET but are less than ST when operating in nominal mode 4. In that excursion B is higher than twice any of the deflections whose peaks are between ET and ST, the algorithm declares the event B as a P-wave, but the next ST_mode will be chosen to be a step higher, i.e., mode 3 so as to provide greater noise immunity.

Figure 5:
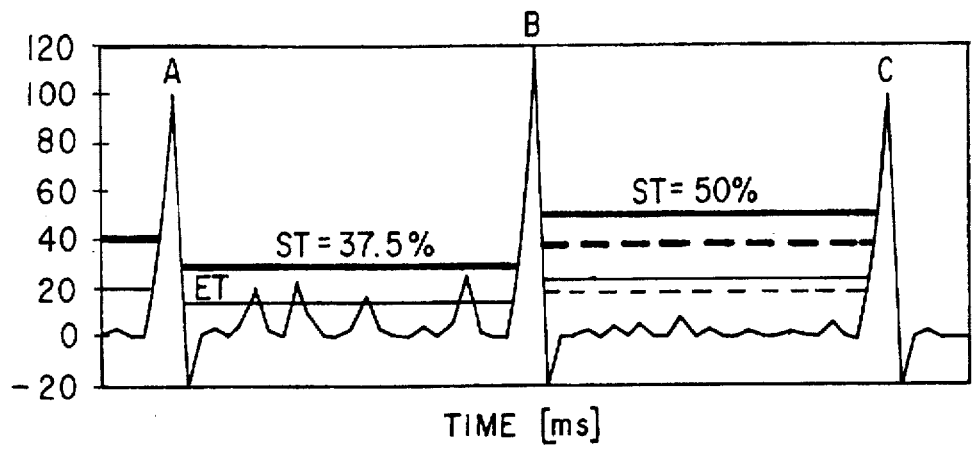
FIG. 5 is an electrogram showing the manner in which the autosense algorithm forces the sensing mode upward in the presence of noise.
Figure 6:
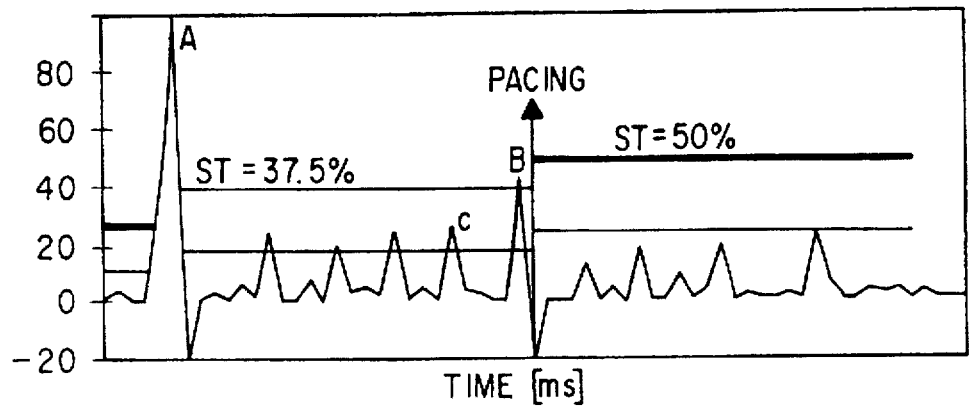
FIG. 6 is an electrogram helpful in understanding the assurance pacing feature of the present invention.

In FIG. 6, a situation is illustrated which is similar to what is depicted in FIG. 5, but the peak ratio of beat B to the highest noise deflection, C, is less than 2. In this case, the algorithm first checks the interval between excursions A and B and compares it to the previous P-to-P interval. If the two intervals differ from one another by less than 75% and the new interval is within a programmed assurance pacing upper limit, the algorithm accepts the beat B as a P-wave, but also applies a pacing pulse within about 70 milliseconds, thereby assuring a stimulated cardiac depolarizing event. If the two P-to-P intervals differ by more than 75%, the autosense algorithm will treat the beat B as noise and will wait for another deflection which is higher than ST until the stimulating pulse is applied. After either pacing or sensing, the algorithm automatically moves one mode step higher to provide increased noise immunity.

Figure 7:
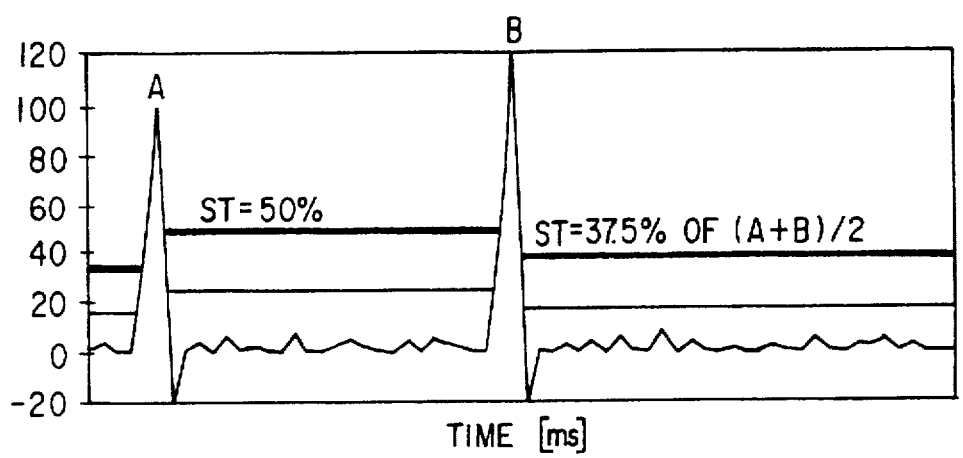
FIG. 7 is an electrogram illustrating the tendency of the autosensing algorithm to cause convergence to a nominal ST_mode.

Referring next to FIG. 7, this electrogram illustrates that the algorithm of the present invention has a tendency to cause convergence of the ST_mode to its nominal mode 4 value during sensed events. It is assumed that intermittent noise had raised the sensing level ST to 50% of the average peak value of A and B and then disappeared. After determining that there is no noise in the interval A to B that exceeds ET, it moves from mode 3 to mode 4.

Figure 8:
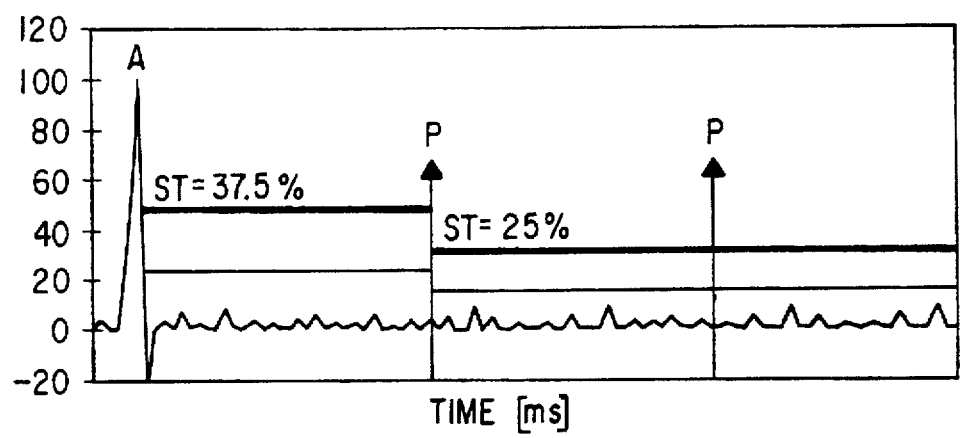
FIG. 8 is an electrogram illustrating the behavior of the autosense algorithm after paced events.

The algorithm operates somewhat differently during pacing events. Referring to FIG. 8, the most desirable pacing events are illustrated. The last intrinsic or sensed beat A is robust and the noise level is below ET that is at 12.5% of the average of two most recent intrinsic beats. In this case, the autosense algorithm maintains a nominal pacing mode at mode 5, i.e., a 25% ST level until it detects any deflections higher than ET. Therefore, even though the two most recent intrinsic beats may have occurred a long time past, the algorithm still uses those intrinsic beats in calculating the ST value. The nominal 25% sensing threshold has been chosen based upon published literature that when using single pass DDD leads, the maximum amplitude reduction of P-waves sensed by those leads is about 75% whereas with positive fixation leads, the amplitude reduction is only about 57% when engaged in exercise as distinguished from being at rest. Thus, during pacing, if there is no deflection detected by the ET threshold, the algorithm will continue to pace and with the nominal ST_mode remaining at mode 5.

Figure 9:
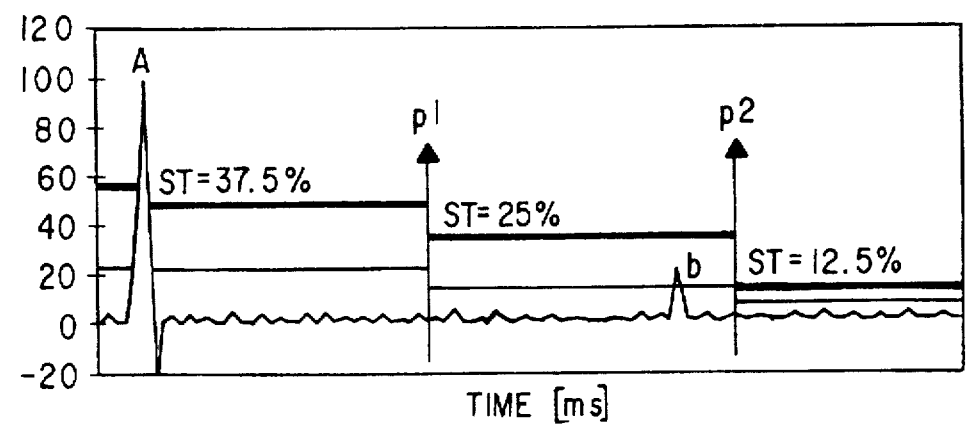
FIG. 9 is an electrogram illustrating the behavior of the autosense algorithm to paced events in the presence of noise.

FIG. 9 illustrates still a further feature of the autosensing algorithm in accordance with the present invention. The algorithm is designed to operate such that if 1, 2 or 3 deflections occur which are outside of a refractory period and which exceed ET but which are less than ST in the interval between p1 and p2, the algorithm will choose mode 6 when establishing the sensing level after issuing the pacing pulse p2 and will determine if any deflections are higher than the new 12.5% value and with a SNR greater than 2. In FIG. 9, deflection b causes the algorithm to choose ST_mode 6. After this mode has been chosen, if no deflections exceed ST until a next pacing moment, the nominal mode 5 value will be selected following the next pacing pulse.

Figure 10:
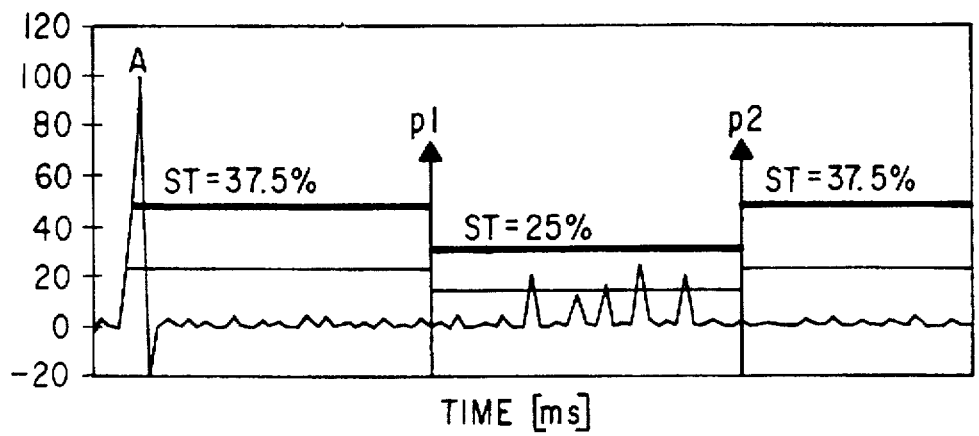
FIG. 10 is an electrogram further illustrating the behavior of the autosense algorithm during pacing events in the presence of noise.

FIG. 10 illustrates a situation similar to that depicted in FIG. 9. However, the number of deflections between p1 and p2 that exceed the ET value is greater than 3. This is indicative of either noise or possible atrial fibrillation. Any such deflections that may have occurred within a refractory period following the issuance of a pacing pulse are not included in the count. After the pacing pulse, p2, is issued, the autosense algorithm selects a ST_mode that is one step greater. One option here is to change the pacemaker mode to VVI. The VII will be maintained until an intrinsic beat detection or the event threshold (ET) during nominal ST_mode of pacing event (mode 5) detects less than four deflections in one pacing interval.

Figure 11:
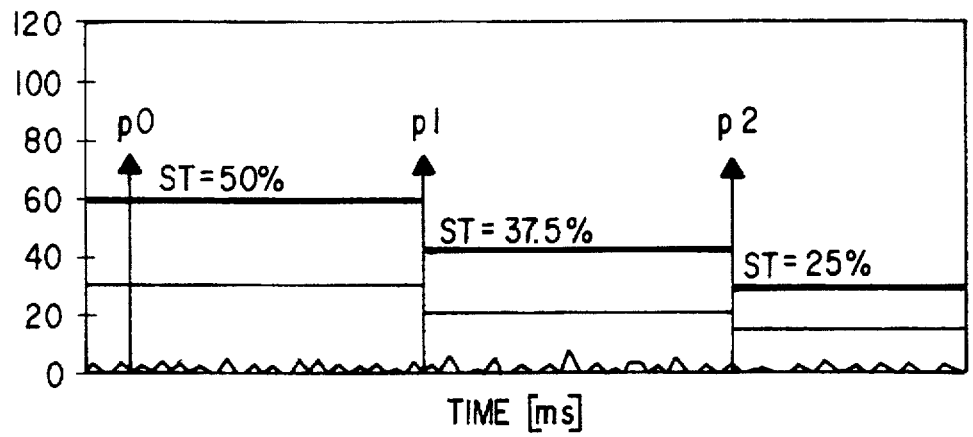
FIG. 11 is an electrogram illustrating the manner in which the autosense algorithm converges to a predetermined nominal sensing threshold during pacing events with minimal noise.

FIG. 11 shows the algorithm's converging tendency to its nominal mode 5 sensing mode during pacing events. Here, after each pacing pulse, the algorithm chooses one step lower mode until the nominal mode 5 is reached.

Figure 12:
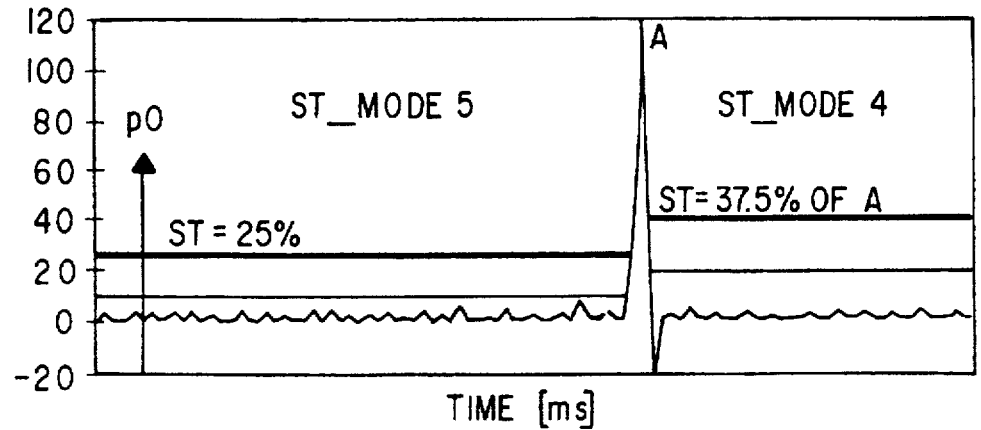
FIG. 12 is an electrogram illustrating a shift in the ST_mode when an intrinsic beat is followed by a paced beat.

The electrograms of FIGS. 12–15 are used to illustrate the behavior of the autosense algorithm when detection of an intrinsic P-wave following a pacing event in mode 5 or mode 6. Each of these cases is provided for to prevent a situation where a very low ST is calculated based on small amplitude beats. In FIG. 12, the intrinsic beat A is shown as following a paced beat p0 and with the current sensing mode at its nominal (mode 5) value. Since the beat A is higher than two times ST, which is at 25%, the algorithm chooses the nominal mode 4 and calculates a new ST by the peaks of the intrinsic beat A and the last such intrinsic beat.

Figure 13:
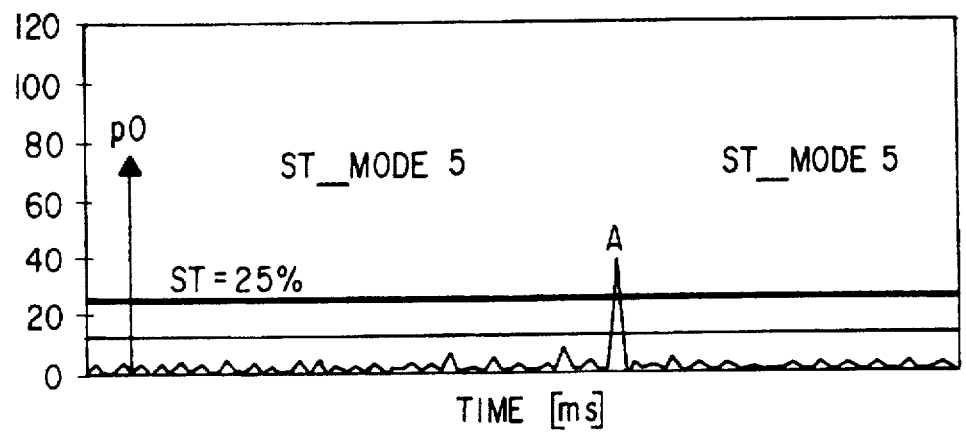
FIG. 13 is an electrogram illustrating the behavior of the autosense algorithm when a low amplitude intrinsic beat is followed by a paced beat.

FIG. 13 shows a situation similar to that of FIG. 12, but with the amplitude of the intrinsic beat A being less than two times the current ST. In this case, the beat is accepted as a P-wave, but the next sensing threshold is not made to depend on the beat A and remains at the same mode level as before. This prevents the next ST from being calculated at too low a value because of the low amplitude of the intrinsic beat A. Were it not for this provision, the autosense algorithm would choose 37.5% of the average of the beat A and the preceding intrinsic beat for a next sensing threshold. The obtained sensing threshold after the beat A will be higher than the previous sensing threshold of 25%, since the amplitude of the proceeding beat is robust. However, if a following beat, after the beat A, has a similar amplitude with it, the next sensing threshold will be calculated based on the two successive low amplitude beats and may be set too low. For example, if it is assumed that the amplitude of beat A and a following beat is about ST of 25% (see FIG. 13), the next ST will be determined at only 9.37%.

Figure 14:
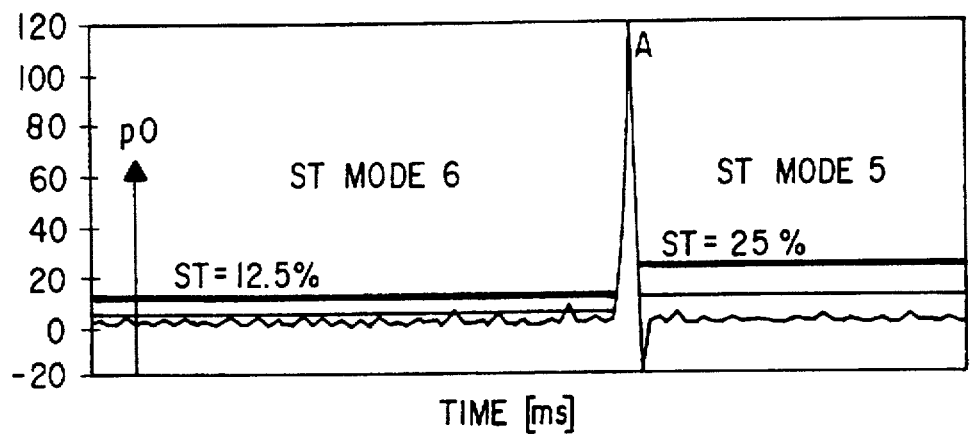
FIG. 14 is an electrogram illustrating the behavior of the autosense algorithm when a high amplitude intrinsic beat is followed by a paced beat.
Figure 15:
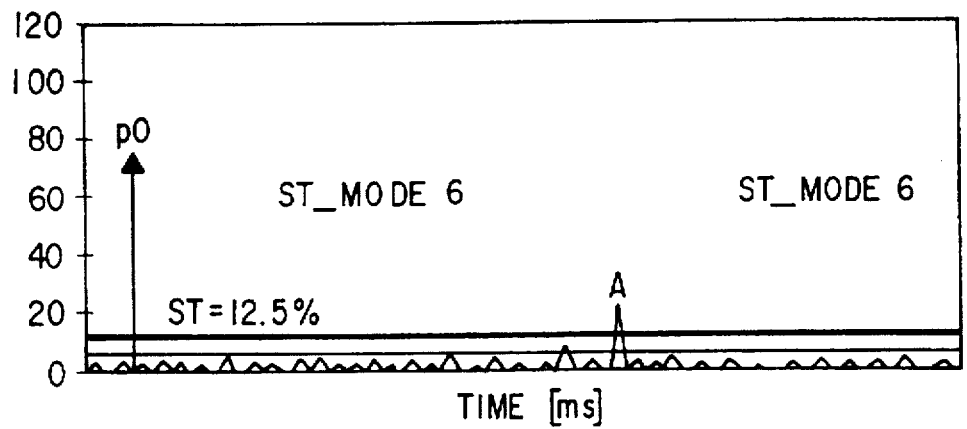
FIG. 15 is an electrogram illustrating the behavior of the autosense algorithm when a relatively low amplitude intrinsic beat is followed by a paced beat.
Figure 16:
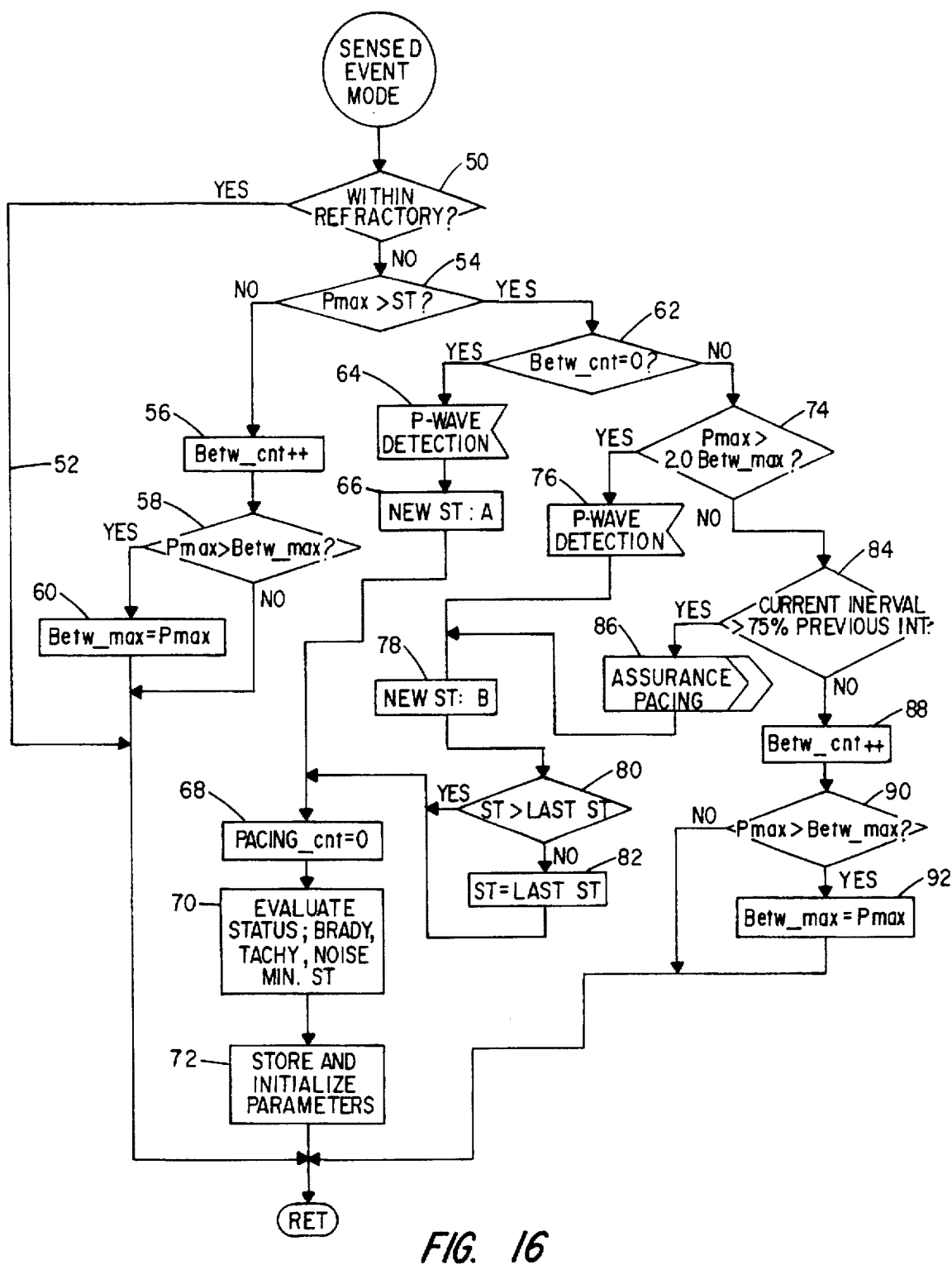
FIG. 16 is a software flow chart of the autosense algorithm of the present invention following detection of a signal exceeding ET.

The situations represented by FIGS. 14 and 15 are quite similar to those illustrated in FIGS. 12 and 13 except that the sensing mode is mode 6 rather than mode 5. FIG. 14 shows that the detected intrinsic beat A is more than twice the current ST level, resulting in a change in the sensing mode to mode 5. FIG. 16 shows the opposite case where the sensing mode remains unchanged because the beat A has an amplitude that is less than twice the existing ST. Although the beat A is accepted as being a P-wave, no change occurs in the ST_mode. That is, it remains mode 6.

Having considered the foregoing examples explaining the mode of operation of the autosense algorithm in accordance with the present invention, the flow charts of FIGS. 16–21 will be more readily understood. The following definitions apply to the symbols used in the flow chart.

| | |
|---|---|
| Pmax = | maximum peak amplitude of an electrogram excursion. |
| Betw_cnt = | counter that accumulates number of deflections in one P-P interval that exceed ET but are less than ST. |
| Betw_cnt$^{++}$ = | increment Betw_Cnt. |
| Betw_max = | the amplitude of a highest peak in one P-P interval. |
| SNR = | signal to noise ratio. |
| Pacing_cnt = | contents of pacing counter. |
| Pacing_cnt$^{++}$ = | increment Pacing_cnt. |

Referring first to FIG. 16, there is shown a software flow chart of a program executed by the microprocessor forming a part of the microprocessor-based controller 28 of FIG. 1. When an electrogram excursion picked up on lead 14 is signal processed by the sense amplifier/filter circuit 12 and converted to a digital quantity by A/D converter 26, a digital quantity proportional to the excursion is applied to one input of the digital comparator 30 and to the microprocessor 28. If the amplitude of that excursion exceeds the event threshold value contained within register 32, the digital comparator 30 will send an interrupt signal to the microprocessor controller, causing it to execute the software routine depicted in FIG. 16. The excursion in question may be a cardiac depolarization event or noise. A first test is made at block 50 to determine whether the event occurred during the device's refractory period following an atrial event or a ventricular event, as the case may be. If the test at 50 indicates that the event did occur within the refractory period, it is determined not to be a depolarization event and control follows branch 52 to return the device to its normal operating mode. If necessary, the branch 52 can be disabled by setting the device's refractory period to 0 ms. If, on the other hand, the test at block 50 determines that the sensed event did not occur within the device's refractory period, a further test is made at block 54 to determine whether the maximum amplitude of the excursion exceeds the sensed threshold (ST). If not, the between counter is incremented each time a deflection occurs in one P—P interval that is greater than ET but less than ST. This operation is represented by block 56 in FIG. 16. Next, a further test is made at decision block 58 to determine whether the peak amplitude of the electrogram excursion in process exceeds the amplitude of the highest peak in one P—P interval. If not, the control returns to the main operating program for the device 10. If the test at decision block 58 shows that the maximum peak amplitude of an electrogram excursion does exceed the amplitude of the highest peak in one P—P interval (Betw__max) then the Betw__max amplitude value is set equal to Pmax (block 60) before control returns to the main program.

If the test at decision block 54 had indicated that the maximum peak amplitude of an electrogram excursion had exceeded the sensing threshold (ST), a test will be made at decision block 62 to determine whether the contents of the between counter (Betw__cnt) is zero, i.e., any noise remains below the event threshold. If so, the Pmax excursion is declared to be a P-wave (block 64) and the subroutine "New ST:A" is then executed (block 66). The flow chart for that subroutine is set out in FIG. 18 and causes convergence of the sensing threshold to its nominal mode 4.

Following execution of the "New ST:A" subroutine, the pacing counter is cleared, which is indicative of the fact that an intrinsic beat has occurred. That is to say, any number but zero in the pacing counter is indicative that the previous event was a paced pulse.

Next, the algorithm evaluates the current status of the device 10 and the new ST value will be compared to the possible minimum ST at the existing sense amplifier gain. If the ST value is lower than the minimum, the minimum ST value will be used for the next ST. After that, the new ST and initial values for various parameters will be loaded into corresponding registers within the microprocessorbased controller. See blocks 70 and 72. The autosense subroutine then exits back to the main program for the microprocessor-based controller 28.

If the test at block 62 had indicated that the Betw__cnt value was other than zero, a further test is made at block 74 to determine whether the current Pmax value is greater than two times the amplitude of the highest peak occurring during a preceding P—P interval. If it is, the excursion is determined to be a P-wave (block 76) and a subroutine called "New ST:B" (block 78) is executed. The flow chart for the subroutine New ST:B is set out in detail in FIG. 19 and is effective to increase the sensing threshold to a value which is one percentage step higher than what had existed and which results in an increase in the noise threshold.

Following execution of that subroutine, a test is made at block 80 to determine whether the execution of the New ST:B subroutine had caused the new sensing threshold so computed to be greater than the immediately preceding ST value. If so, control loops back to the input of block 68 and steps 68, 70 and 72 previously described are carried out. If the test at block 80 had revealed that the execution of the subroutine represented by block 78 and shown in FIG. 19 had resulted in a ST greater than the immediately preceding one, then the ST value is set equal to the preceding ST value before control loops back to the input of block 68.

Had the test at decision block 74 indicated that the maximum excursion was not greater than twice the amplitude of the highest peak in the preceding P—P interval, a test is made at block 84 to determine whether the current P—P interval is longer than 75% of the preceding P—P interval and is within the assurance pacing upper limit. If so, assurance pacing takes place (block 86).

By way of explanation, in some sensing situations, a deflection may be encountered which seems to have more chance of being a P-wave compared to other deflections, but which is difficult to be accepted as a P-wave in low SNR electrograms or abnormally low amplitude electrograms. For these kinds of deflections, the algorithm of the present invention will issue a pacing pulse within approximately 100 milliseconds of the excursion in order to make the event a definite cardiac depolarization. If it had been noise and it was followed within the 100 millisecond interval by an intrinsic beat, the subsequently applied assurance pacing pulse would have no effect on the patient because it would be firing into the heart's refractory period.

Had the test at decision block 84 revealed that the current P—P interval was less than 75% of the previous interval, the between counter (Betw__cnt) is incremented (block 88) and a further test is made at decision block 90 to determine whether the electrogram excursion exceeds the amplitude of the highest peak detected during the preceding P—P interval. If so, the Betw__max value is set equal to Pmax (block 92), thus declaring noise and because no evaluation nor initialization will be required, control immediately exits to the main routine that had been interrupted by the occurrence of the sensed event exceeding the threshold value contained in the threshold register 32 in the device 10 of FIG. 1.

Figure 17:
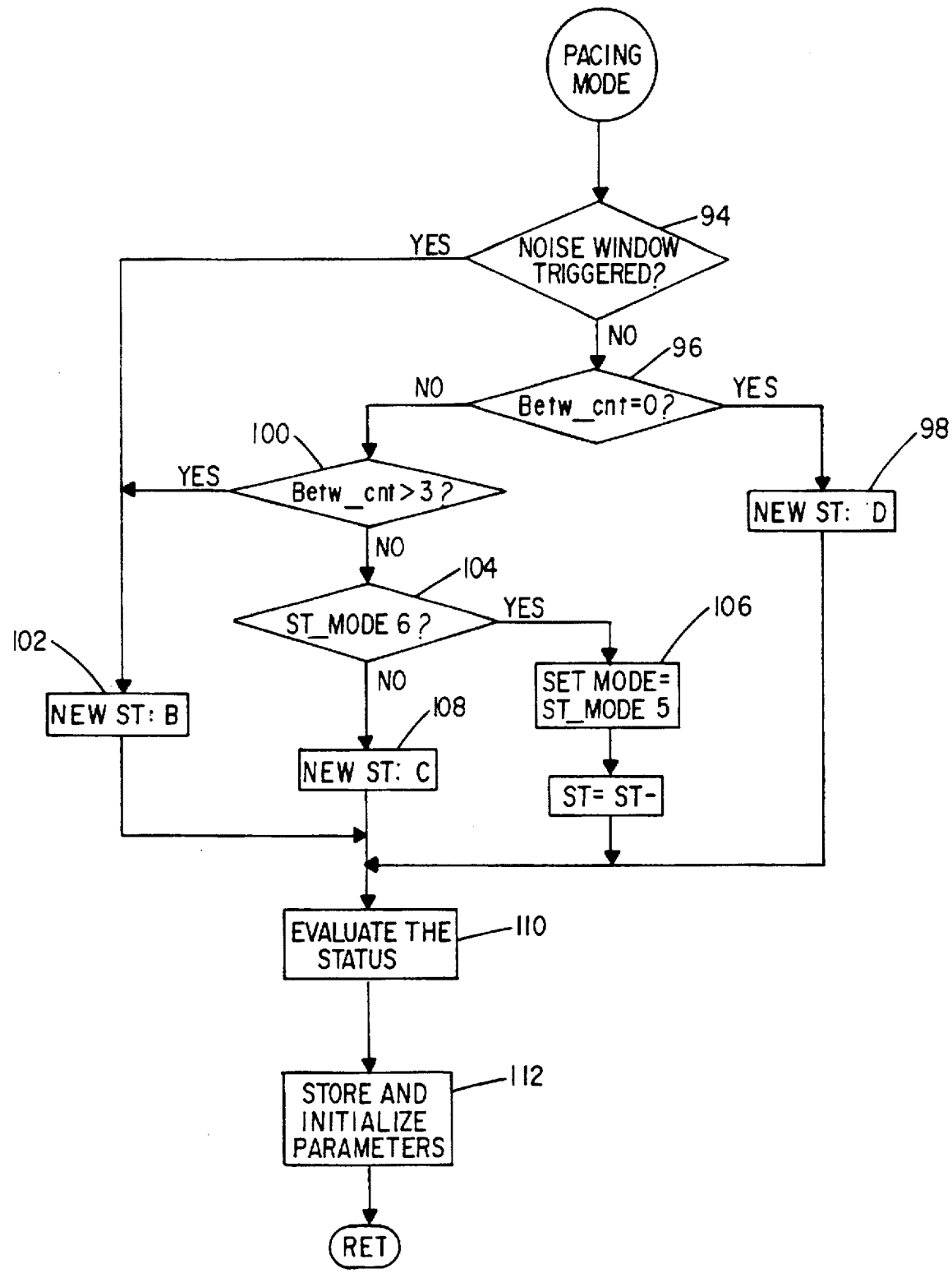
FIG. 17 is a software flow chart of the autosense algorithm of the present invention following a paced event.
Figure 19:
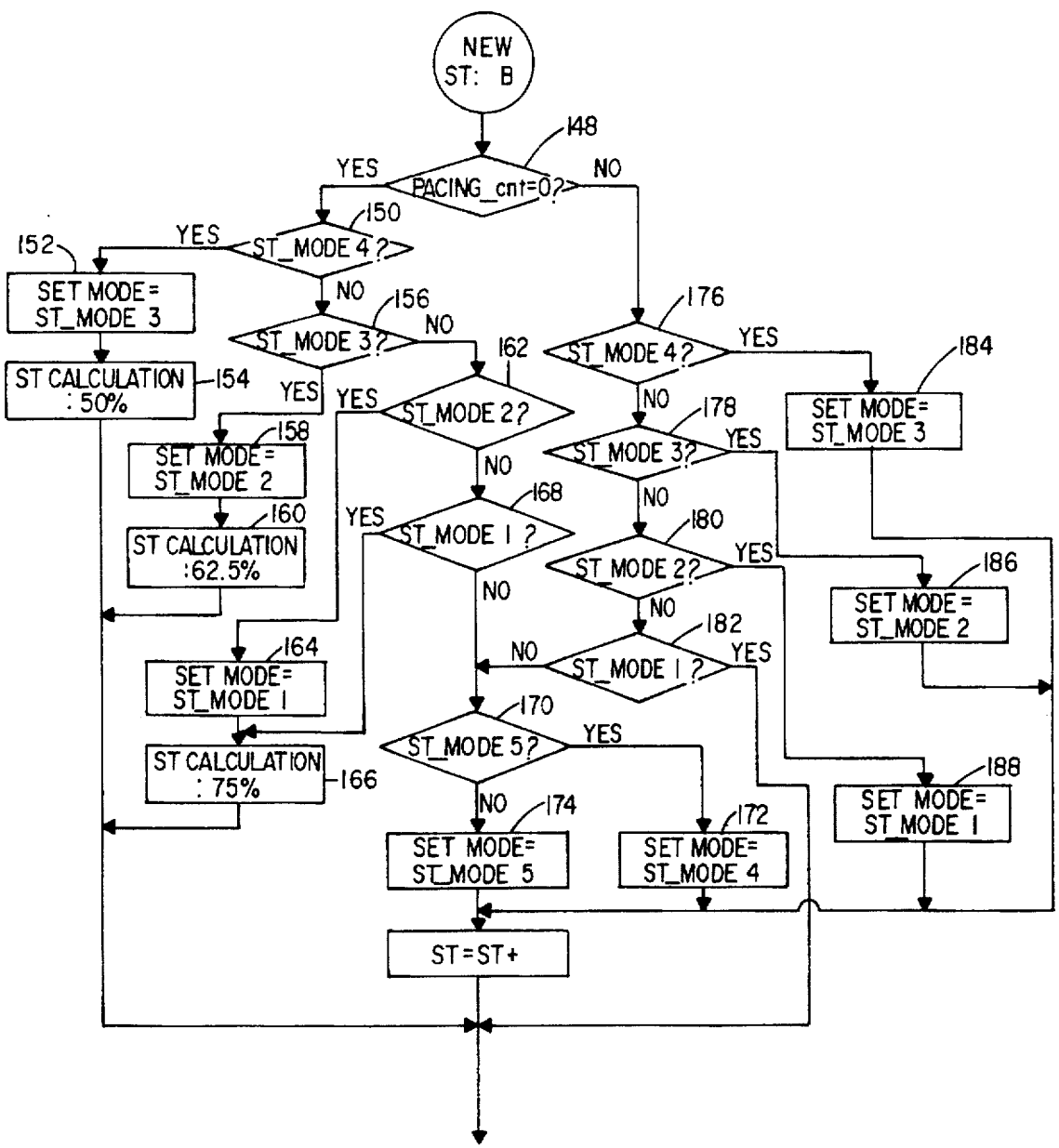
FIG. 19 is a software flow chart for the subroutine New ST:B in the flow charts of FIGS. 16 and 17.
Figure 21:
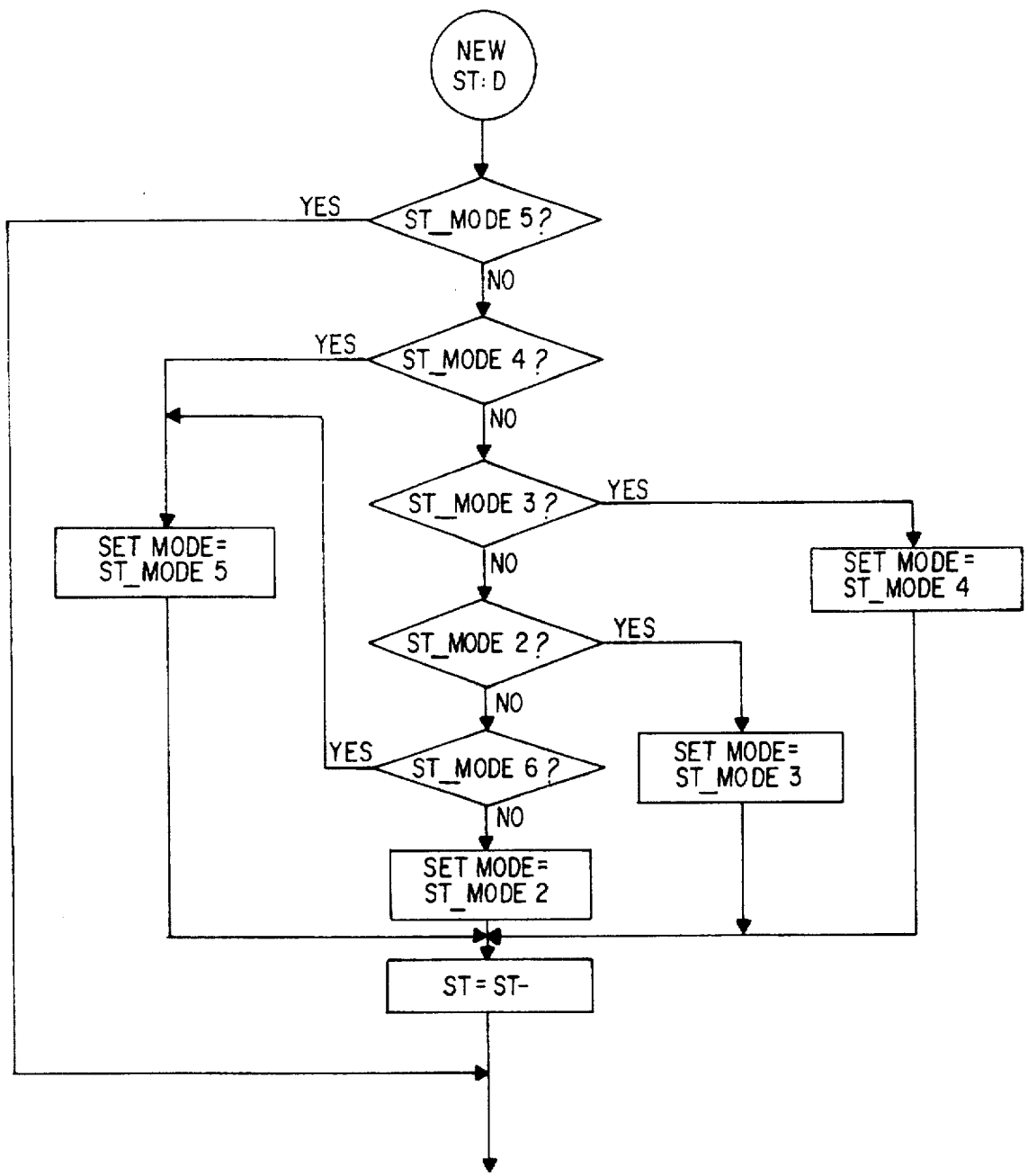
FIG. 21 is a software flow diagram of the subroutine New ST:D embodied in the flow chart of FIG. 17.

The autosense algorithm of the present invention is also dependent upon whether the electrogram excursions correspond to intrinsic beats or paced beats. FIG. 17 is a flow diagram for a demand pacemaker where naturally occurring atrial or ventricular beats are missing and the pacemaker device 10 is supplying pacing pulses to the heart. Considering the case where a p—p interval counter within the microprocessor 28 times out, an interrupt is delivered to the microprocessor 28 which then issues a pacing pulse over the leads 14 to the heart. The pacing device in which the present invention finds use provides for a serial noise window following a refractory period. Those skilled in the art recognize that if noise signals are detected during the window, the window will be reinitiated for another period. Decision block 94 tests whether the noise window has been retriggered and, if so, the subroutine New ST:B is again called. See block 102. As will be explained in greater detail below when FIG. 19 is considered, that subroutine causes the ST__mode to advance one step. If the noise window is not retriggered, the autosense algorithm checks at decision block 96 to determine if Betw__cnt is zero or not. Assuming that the Betw__cnt is zero, this means that no deflection had occurred in the P—P interval that is higher than ET, but less than ST and a subroutine "New ST:D" (block 98) is called. The detailed flow chart for this subroutine is illustrated in FIG. 21.

The function of the New ST:D procedure is to cause convergence of the ST__mode of pacing event to its nominal value, which in this case is ST__mode 5 where 25% is the multiplying factor to be applied to the average maximum peak amplitudes of the current and proceeding beats in arriving at ST. If the current ST__mode is higher than the nominal mode 5, the subroutine illustrated by the flow diagram of FIG. 21 will move the mode one step closer to the nominal for a paced beat.

It is important to note that the ST will be calculated based on the two last intrinsic beats. That is, if the current ST__mode is not mode 5 or if ET detects noise signals, the next ST will be obtained by selecting a different ST__mode while the average of the two preceding intrinsic beats remains unchanged. In the flow charts of FIGS. 17–21, this step is represented by the blocks labeled ST=ST+ or ST=ST− and represent the ST__mode changes with the unchanged average amplitude of the preceding two intrinsic beats. As is perhaps apparent, ST=ST+ represents the case where the mode is stepped up by one while ST=ST− selects the next lower mode number.

With continued reference to FIG. 17, if the contents of the between counter is not zero, the autosense algorithm will next check the number of deflections that exceed ET but are less than ST. This operation is represented by decision block 100. If the contents of the between counter are greater than 3, the autosense algorithm treats the excursions as noise and will step up the ST__mode in accordance with the New ST:B subroutine.

Figure 20:
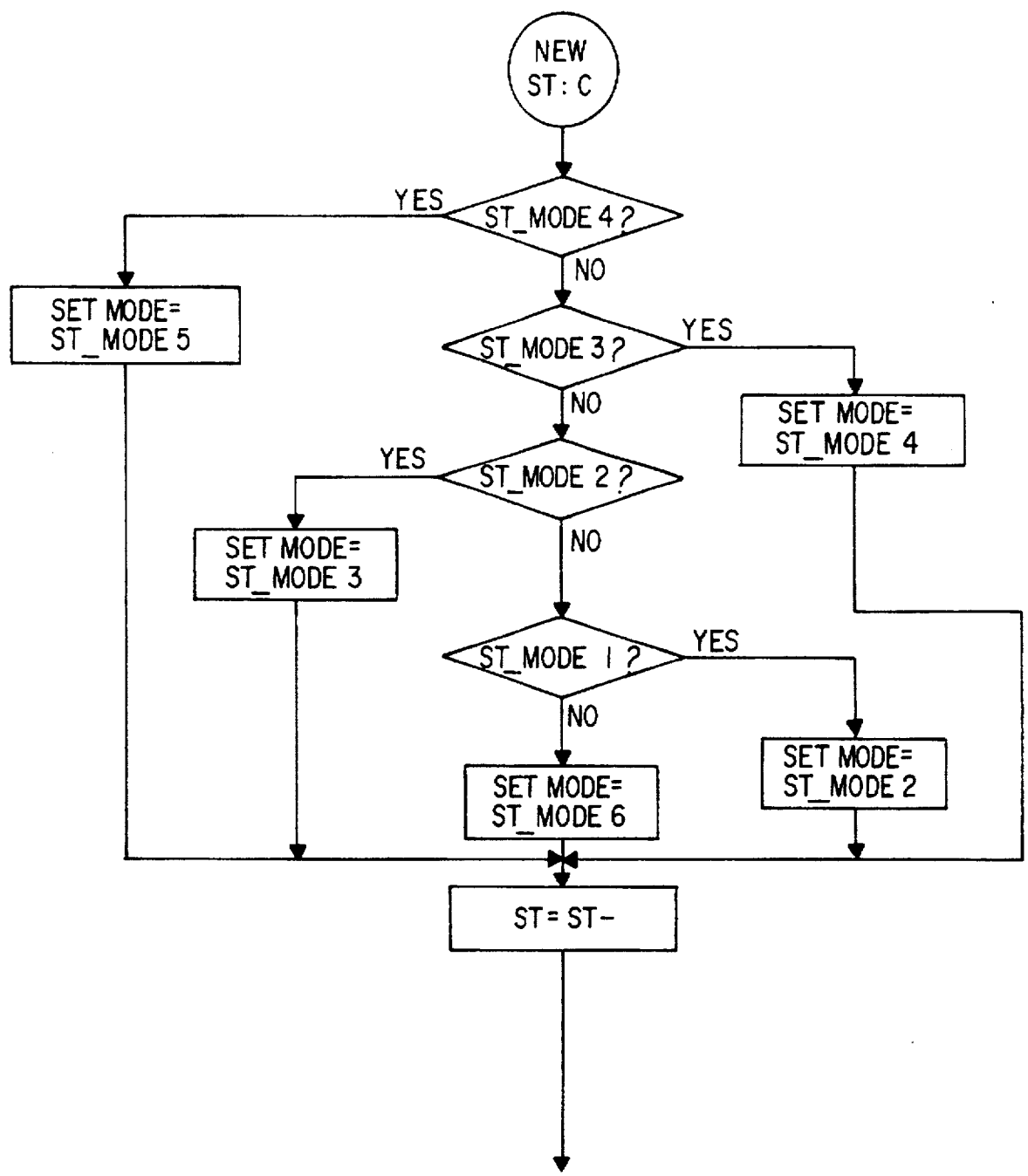
FIG. 20 is a software flow diagram for the subroutine New ST:C set out in the flow chart of FIG. 17.

If the contents of the between counter are three or less, the algorithm checks the current ST_mode to determine if it is mode 6. See decision block 104. If it is, the mode is set to the nominal mode 5, but if not, a further subroutine called "New ST:C" (block 108) will be executed. The flow diagram for the subroutine New ST:C is illustrated in FIG. 20. The function of this subroutine procedure is to choose a ST_mode one step lower than that presently involved.

The difference between the subroutines 108 and 98 is that mode 6 will be chosen if the current mode is mode 5. New ST:D operates so that if mode 5 is already present, it remains unchanged.

As in the case of the flow diagram of FIG. 16, blocks 110 and 112 operations result in an evaluation of current status and the initialization of various registers prior to the return to the main routine.

Figure 18:
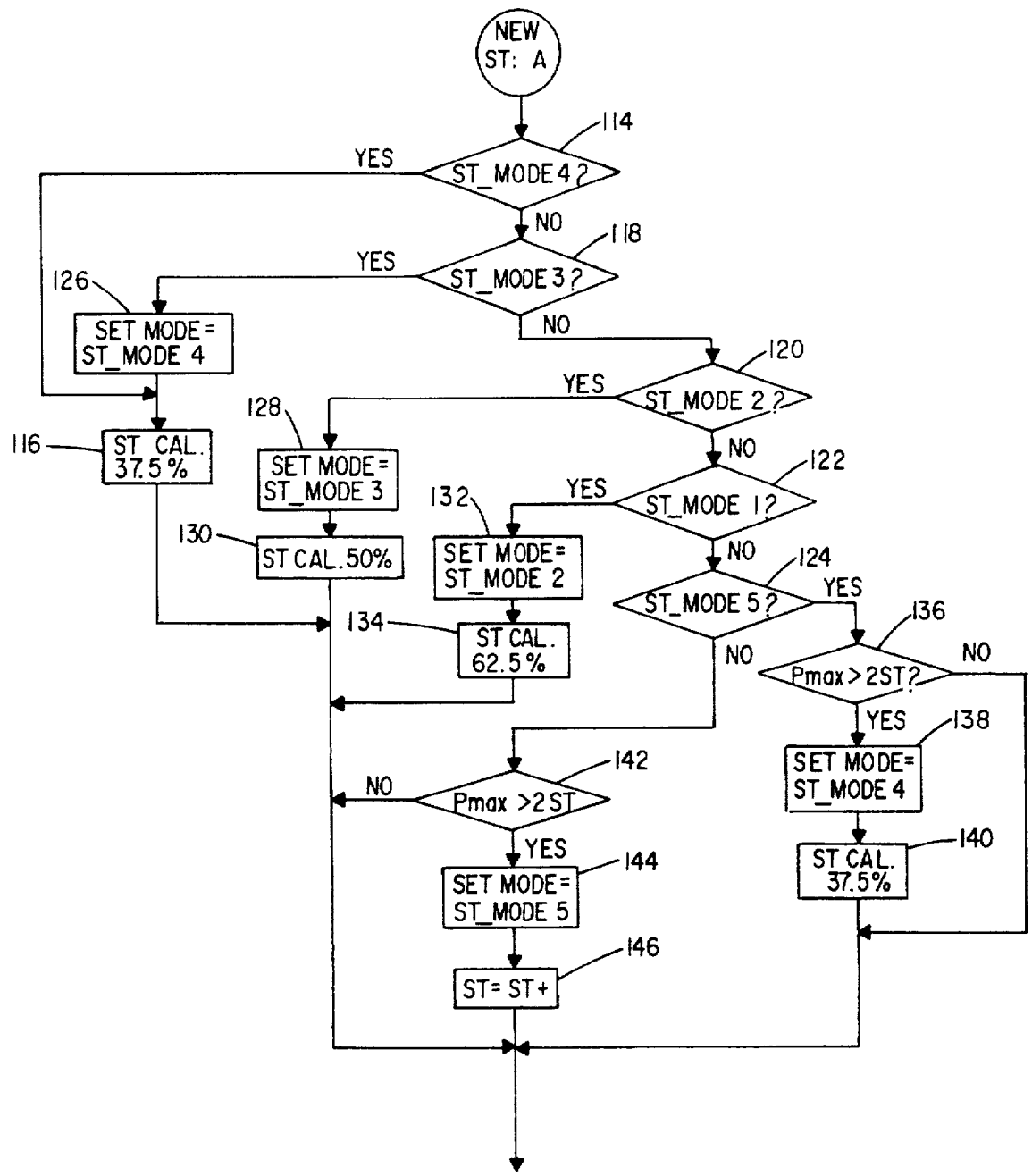
FIG. 18 is a software flow diagram of the New ST:A subroutine embodied in the flow chart of FIG. 16.

Having described the autosense algorithm for both sensed beats and paced beats with the aid of the flow diagrams of FIGS. 16 and 17, respectively, attention will next be given to the subroutines New ST:A, B, C and D, that are called in the main routines. Referring to FIG. 18, when new ST:A is called, a test is made at decision block 114 to determine if ST_mode 4 is currently active. If so, the ST calculation for the next interval will remain at 37.5% (block 116) and control returns directly to the autosense routine. If the test at decision block 114 had revealed that the mode was other than mode 4, then a further test is made at decision block 118 to determine if mode 3 is extant. If not, further checks are made at decision blocks 120, 122 and 124 until the current mode involved is determined. If it had been mode 3, the operation at block 126 is carried out to set the new mode to the nominal value, mode 4. Likewise, if the current mode had been mode 2, it would be advanced at operation block 128 to mode 3 and the calculation of the next ST value would be based upon 50% of the average peak amplitude of the current and preceding beat. See block 130. A finding that the current mode is mode 1 at block 122 similarly causes the new mode to be set at mode 2 (block 132) causing the next ST to be based upon 62.5% of the average peak value of the current and preceding deflections.

If the test at decision block 124 had revealed that ST_mode 5 had been in play, a test is made at decision block 136 to determine whether the maximum peak amplitude of the electrogram excursion is greater than two times the existing sensing threshold. If not, no change is made in the sense threshold level. However, if Pmax is greater than twice the sensing threshold, the ST_mode is decreased by one to mode 4, i.e., the nominal mode (block 138) and the new sensing threshold, ST, is based upon 37.5% of the average peak amplitude of the current and immediately preceding electrogram deviation. See block 140.

Had the test at decision block 124 indicated that the existing ST_mode was not equal to 5, it necessarily means, by process of elimination, that mode 6 is in play. In this event, a test is made at decision block 142 to determine whether Pmax is greater than two times ST and, if so, the mode is decremented by one to ST_mode 5 (block 144). This operation is followed by operation 146 which selects the sensing threshold that is one step higher percentagewise without considering a new Pmax, if detected. The effect of this is to lower the noise threshold.

Referring next to FIG. 19, the subroutine New ST:B will be explained. This subroutine is called in both the autosense algorithm flow charts of FIGS. 16 and 17. Referring to FIG. 16, if the number (Betw_cnt) is other than zero and the test at block 74 shows that a current Pmax is at least two times higher than the highest peak occurring in the preceding P—P interval, that peak is identified to the microprocessor as a P-wave, followed by execution of the subroutine of FIG. 19. It calculates a new ST by choosing a ST_mode that is one step higher, i.e., a higher percentage of ST. If the pacing counter is zero as determined at decision block 148, the test at block 150 determines whether the current ST_mode is mode 4. If so, the mode will be set to mode 3 at operation block 152 causing a 50% factor to be used for the next ST calculation (block 154).

Had the test at block 150 shown that the current mode was not mode 4, a test is made at decision block 156 to determine whether the current mode is mode 3. If so, the mode for the next interval is decreased by one to mode 2 (block 158) such that a factor of 62.5% is applied to the average peak amplitude of the current and immediately preceding excursion in arriving at the ST. This is represented by block 160.

If the tests performed at decision blocks 150 and 156 had shown that the current mode was other than mode 4 and mode 3, a further test is made at decision block 162 to assess whether the current mode is mode 2. If so, the mode is lowered by one (block 164) and the next ST calculation is based upon a 75% factor (block 166).

If the tests at decision blocks 150, 156 and 162 had all produced a "no" response, a further test is made at decision block 168 to test for ST_mode 1. If the current mode had been mode 1, the 75% factor would again be used for the succeeding ST calculation. If neither mode 4, 3, 2 or 1 had been currently in play, the test at decision block 170 determines whether mode 5 is involved. If so, the mode for the next interval is set to mode 4 (block 172) and ST is chosen to be one step higher percentagewise irrespective of the new Pmax amplitude, if detected. Had the test at decision block 170 been "no", mode 6 must have been in play and the operation at block 174 causes the new mode to drop to ST_mode 5.

If one or more paced beats had occurred, such that the test at decision block 148 indicated a value other than zero in the pacing counter, a test is made at decision blocks 176, 178, 180 and 182 to determine whether the current ST_mode was mode 4, 3, 2 or 1, respectively. If mode 4, the operation at block 184 is carried out to change to mode 3. Likewise, had the current mode been mode 3, it is changed to mode 2 (block 186) and if it had been mode 2, it is changed to mode 1 (block 188). If neither mode 4, 3, 2 or 1 is in play, then the test at decision block 170 again takes place, with the same outcome as before.

Having described subroutine New ST:A and New ST:B in detail, it is believed unnecessary to "walk through" the subroutines of FIGS. 20 and 21. Suffice it to say, the operations ST=ST− selects the sensing threshold which is one step lower percentagewise by using the two most recent beats.

Using the autosense algorithm of the present invention accommodates significant variations in the amplitudes of cardiac depolarization signals, both P-wave and R-wave. This permits the use of both positive fixation leads and single pass VDD leads with a much lower incidence of malsensing, irrespective of whether the patient is active or at rest.

The out-of-sense algorithm of the present invention finds particular use where a cardiac depolarization event, e.g., a P-wave is not particularly robust. It is envisioned that a conventional arrangement of a comparator having a fixed, programmable threshold may be included to determine whether such a P-wave is sufficiently robust to allow conventional sensing. Then, only if the cardiac depolarization event falls below this threshold will the autosense algorithm of the present invention be called into play. For example, if a patient exhibits a P-wave amplitude higher than, say, 3.7 mv, a fixed sensing threshold of, say, 0.75 mv. However, when the P-wave amplitude of the patient becomes less than the 3.7 mv amplitude, this condition is detected and the autosense algorithm of the present invention will be initiated in the microprocessor-based controller to provide the further ET threshold and the assurance pacing functions automatically for improved sensing performance.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of automatically adjusting a sensing threshold (ST) in a cardiac rhythm management device to distinguish cardiac depolarization events from noise in cardiac electrogram signals, the cardiac rhythm management device being of the type having means for sensing cardiac electrogram signals, a microprocessor-based controller coupled to receive the sensed electrogram signals, and means controlled by the microprocessor-based controller for applying cardiac stimulation pulses to a patient's heart in response to control signals from the microprocessor-based controller on a beat-to-beat basis comprising the steps of:

(a) calculating in the microprocessor-based controller an average of peak amplitudes of two most recent cardiac electrogram signals;

(b) establishing an ST value equal to a predetermined percentage of the average of peak values calculated in step (a);

(c) establishing an event threshold (ET) value equal to a predetermined percentage of the ST value established in step (b);

(d) comparing a peak amplitude of a subsequent cardiac electrogram signal to the ET value established in step (c);

(e) interrupting the microprocessor of the microprocessor-based controller when the subsequent cardiac electrogram signal exceeds the ET value to initiate a programmed subroutine for determining if the subsequent cardiac electrogram signal also exceeds the ST value and, if so, identifying that subsequent cardiac electrogram signal as a cardiac depolarization event rather than noise; and (f) repeating steps (a) through (e) to calculate new ST and ET values to be used in distinguishing a next cardiac depolarization event from noise.

2. The method as in claim 1 wherein the predetermined percentage referred to in step (c) is 50%.

3. The method as in claim 1 wherein the predetermined percentage referred to in step (b) is dependent upon noise levels in the cardiac electrogram signal in the interval between a current cardiac depolarization event and an immediately preceding cardiac depolarization event.

4. The method as in claim 1 wherein the programmed subroutine further determines if the subsequent cardiac electrogram signal that exceeds (ST) falls outside of a refractory interval associated with an immediately preceding detected cardiac depolarization event.

5. The method as in claim 4 and further including the step of determining in the microprocessor whether the subsequent cardiac electrogram signal falling outside of the refractory period is of an amplitude exceeding ST in identifying that the subsequent cardiac electrogram signal is a cardiac depolarization event rather than noise.

6. The method as in claim 5 and further including the step of:

(a) applying a cardiac stimulating pulse within a fixed time of a preceding electrogram excursion when a maximum peak amplitude of that electrogram excursion is less than twice the amplitude of a highest peak excursion occurring during a current p-to-p interval and said p-to-p interval exceeds a predetermined percentage of an immediately preceding p-to-p interval.

7. The method as in claim 6 wherein the predetermined percentage referred to in claim 6 is 75%.

8. The method as in claim 6 wherein the fixed time is in a range of from about 70 ms to 100 ms.

9. The method as in claim 1 wherein the predetermined percentage applied to the average of peak values calculated in step (a) is selected from a set of predetermined percentage values, the selected percentage value to be used being dependent upon the amplitude of the subsequent electrogram signal relative to an existing ST value.

10. The method as in claim 9 wherein the predetermined percentage applied to the average of peak values calculated in step (a) is selected from a set of predetermined percentage values where the selected percentage value is further dependent upon whether a current cardiac electrogram signal is an intrinsic beat or a paced beat.

11. The method of claim 9 wherein the predetermined percentage value applied to the average of peak values calculated in step (a) is selected from a set of predetermined percentage values, the selected percentage value to be used being further dependent upon a count of a number of noise deflections occurring in a preceding p-to-p interval.

12. In an implantable cardiac rhythm management device of the type including a pulse generator, a microprocessor-based controller for controlling activation of the pulse generator, lead means for applying electrogram signals comprising both cardiac depolarization signals and noise to the microprocessor-based controller, the improvement comprising:

(a) comparator means for comparing the electrogram signals to a predetermined event threshold (ET) and generating an interrupt control signal to the microprocessor when electrogram signals exceed ET;

(b) means in the microprocessor-based controller responsive to the interrupt signal for executing programmed subroutine, establishing a sensing threshold, ST, which is a predetermined percentage of the average maximum peak values of two most recent cardiac depolarization signals; and (c) means for setting the ET of the comparator to a value which is a predetermined fraction of ST.

13. The implantable cardiac rhythm management device of claim 12 wherein the predetermined percentage is a selected one of a plurality of possible percentage values, the selected one being determined by the maximum peak amplitude of a current electrogram excursion comprising a cardiac depolarization signal and a number of noise excursions exceeding the current ET.

14. The implantable cardiac rhythm management device of claim 12 wherein the predetermined percentage is a selected one of a plurality of possible percentage values, the selected one being dependent on whether a current electrogram excursion is an intrinsic event or a paced event.

15. The implantable cardiac rhythm management device of claim 13 wherein the plurality of possible percentage values comprise 75%, 62.5%, 50%, 37.5%, 25% and 12.5%.

16. The implantable cardiac rhythm management device of claim 12 wherein said predetermined fraction is ½.

* * * * *